United States Patent
Goumri-Said et al.

(10) Patent No.: US 11,931,378 B2
(45) Date of Patent: *Mar. 19, 2024

(54) METHOD AND PROCESS TO MAKE CHITOSAN-DOPED STRONTIUM OXIDE NANOCOMPOSITE FOR BACTERICIDAL APPLICATIONS

(71) Applicant: Alfaisal University, Riyadh (SA)

(72) Inventors: Souraya Goumri-Said, Riyadh (SA); Mohammed Benali Kanoun, Riyadh (SA); Salamat Ali, Lahore (PK); Junaid Haider, Tianjin (CN); Ali Haider, Lahore (PK); Muhammad Ikram, Lahore (PK)

(73) Assignee: Alfaisal University, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/551,882

(22) Filed: Dec. 15, 2021

(65) Prior Publication Data

US 2023/0190788 A1 Jun. 22, 2023

(51) Int. Cl.
| | | |
|---|---|---|
| *A61K 33/14* | (2006.01) | |
| *A61K 9/08* | (2006.01) | |
| *A61K 47/02* | (2006.01) | |
| *A61K 47/36* | (2006.01) | |
| *A61P 31/04* | (2006.01) | |
| *C01F 11/24* | (2006.01) | |
| *C08L 5/08* | (2006.01) | |

(52) U.S. Cl.
CPC ............... *A61K 33/14* (2013.01); *A61K 9/08* (2013.01); *A61K 47/02* (2013.01); *A61K 47/36* (2013.01); *A61P 31/04* (2018.01); *C01F 11/24* (2013.01); *C08L 5/08* (2013.01)

(58) Field of Classification Search
None
See application file for complete search history.

(56) References Cited

PUBLICATIONS

Ikram et al. 2 Journal of Nanostructure in Chemistry vol. pp. 933-950 available on Line Oct. 12, 2021 (Year: 2021).*
Tomke et al. International Journal of Biological Macromolecule 149, pp. 989-999, 2020. (Year: 2020).*

* cited by examiner

*Primary Examiner* — Jana A Hines
*Assistant Examiner* — Khatol S Shahnan Shah
(74) *Attorney, Agent, or Firm* — Geeta Kadambi; RIDDHI IP LLC (57) ABSTRACT

Strontium oxide (SrO) nanoparticle and various concentrations of chitosan (CS)-doped SrO nanocomposite were synthesized via co-precipitation method. A variety of characterization techniques including were done for characterizing and qualifying the nanocomposite. X-ray powder diffraction affirmed cubic and tetragonal structure of SrO nanoparticle and CS-doped SrO nanocomposite with a decrease in crystallinity upon doping. Fourier transform infrared spectrum endorsed existing functional groups on CS/SrO surfaces while d-spacing was estimated using high resolution Transmission electron microscopes images. UV-Visible and Photoluminescence spectroscopy spectra showed an increase in band gap energies with an increase in doping concentration. Elemental composition of CS-doped SrO nanocomposite deposited with different doping concentrations was studied using Energy dispersive Spectroscopy. Addition of chitosan resulted in the formation of nanocomposite and rod-like structures that led to enhanced catalytic activity during methylene blue ciprofloxacin degradation in the presence of reducing agent sodium borohydrate at various pH conditions.

14 Claims, 12 Drawing Sheets

METHOD AND PROCESS TO MAKE CHITOSAN-DOPED STRONTIUM OXIDE NANOCOMPOSITE FOR BACTERICIDAL APPLICATIONS

FILED OF TECHNOLOGY

A method and process to make and use chitosan-doped strontium oxide nanocomposite for bactericidal applications is described.

BACKGROUND

Infections are pivotal concerns that, if not treated effectively, may be lethal, depending on the location of the wound. Thus, it is critical to have bactericidal action against both gram-positive and gram-negative bacteria cells as *Staphylococcus aureus* (*S. aureus*) and *Escherichia coli* (*E. coli*) are two of the most frequent bacteria that have developed a high level of antibiotic resistance. These bacteria are capable of causing life-threatening illnesses such as pneumonia, endocarditis, and sepsis. Antimicrobial resistance (AMR) is a term that refers to a microorganism's capacity to withstand the effects of treatment that was formerly effective in treating the microbes. Bacterial resistance may be acquired or adopted natural. Natural resistance occurs when bacteria's characteristics block the activity of a particular antibiotic. Antibiotics that are intended to bind to particular receptors on bacterial cells are rendered ineffective if the bacterial species lacks the receptors, but acquired resistance occurs as a consequence of the bacterial species' genetic composition changing in such a way that antibiotic activity is reduced. Bacterial population is naturally capable of acquiring resistance to antibiotics and metals, which increases the potential for sickness and produces health issues. Drug resistance in bacteria results in the poor treatment of a variety of diseases. As a result, increasing focus has been paid to the creation of stable antibacterial nanomaterial for human welfare.

SUMMARY

The instant declaration describes a method and process of making strontium oxide (SrO) nanoparticle. In another embodiment adding SrO nanoparticle with chitosan and making a chitosan (CS)-doped SrO nanocomposite by co-precipitation method is described. In one embodiment, the chitosan (CS)-doped SrO nanocomposite is used for reducing bacterial infection in cells. In one embodiment, CS-doped SrO nanocomposite with various concentrations of CS (0, 2, 4 and 6 wt %) is added to act as an antibacterial agent to curb inhibit the growth of Gram+ive and Gram−ive bacetrai. In one embodiment, a method of making a CS-doped SrO nanocomposite to render sufficient bactericidal activities of prepared samples were evaluated against *S. aureus* and *E. coli* bacteria is disclosed. In one embodiment, formation of nanoparticles and rod-like structures of chitosan (CS)-doped SrO nanocomposite showed enhanced bactericidal activity during against bacterial solutions are disclosed.

In one embodiment a process of making SrO nanoparticle from strontium (Sr) precursor is described. In one embodiment, strontium chloride hexahydrate is used as a chemical precursor to make SrO nanoparticles in powder form. In one embodiment, a process strontium chloride hexahydrate is dissolved in distilled water and magnetically stirred for 2 hours. In another embodiment, adjusting a pH of the dissolved solution of strontium chloride hexahydrate to a specific pH such as pH 12 is done and by adding sodium hydroxide solution for 2 hours to form a precipitate of a strontium chloride hexahydrate nanoparticle in solution is described.

Strontium chloride hexahydrate nanoparticle in solution is then centrifuged to collect a pellet of the precipitate of the strontium chloride hexahydrate nanoparticle. Subsequently the pellet of the strontium chloride hexahydrate nanoparticle is heated at 120° C. for 24 hours to obtain a powder of strontium chloride hexahydrate nanoparticles; preparing a strontium chloride hexahydrate nanoparticle solution using the powder of strontium chloride hexahydrate nanoparticles in distilled water with various concentrations of a chitosan the specific pH using a specific basic solution to create a CS-doped SrO nanocomposite; the resultant product is used as antibacterial agent in the cell.

In one embodiment, a process of making a CS-doped SrO nanocomposite by mixing water and a strontium chloride hexahydrate and stirring the mixer for 2 hours to make a solution of the strontium chloride hexahydrate and in order to form a precipitate of a strontium chloride hexahydrate nanoparticle in solution by adjusting a pH of the solution of strontium chloride hexahydrate to a specific pH at 12 by adding sodium hydroxide solution for 2 hours and stirring is performed. Once the pellet is formed, in one embodiment, collecting a pellet strontium chloride hexahydrate nanoparticle by centrifuging a strontium chloride hexahydrate nanoparticle in solution and making a powder of strontium chloride hexahydrate nanoparticles by heating the pellet of the strontium chloride hexahydrate nanoparticle at 120° C. for 24 hours and grinding the heated pellet is done.

In one embodiment a process of preparing a strontium chloride hexahydrate nanoparticle solution using the powder of strontium chloride hexahydrate nanoparticles in distilled water with various concentrations of a chitosan the specific pH using a specific basic solution to create a CS-doped SrO nanocomposite is done. In one embodiment, antibacterial activity was exhibited by the said CS doped SrO nanocomposite.

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

In the instant disclosure, a method and process of making a CS-doped SrO nanocomposite are described. The instant invention the CS-doped SrO nanocomposite is characterized by measuring structural properties and phase compositions. In another embodiment, a method to inhibit bacterial growth using the CS-doped SrO nanocomposite is described. In one embodiment, a process to make and use the CS-doped SrO nanocomposite is described to inhibit bacterial growth. Antimicrobial medications based on nanomaterial are more functional and robust in hostile environments. Chitosan is often used as an antibacterial ingredient combined with other polymers to create antibacterial films. Chitosan inhibit and repress microbial activity through an electrostatic charge interaction between polycationic chitosan molecules (amino groups) and the negative charges at bacterial surface. Chitosan, on the other hand, was not employed in nanoparticles form. Due to the nanoparticle size of chitosan, they have unique physicochemical characteristics as large surface area and strong reactivity, which may boost the charge interaction on the microbial surface and result in superior antibacterial effect.

Strontium is an alkaline earth metal with a highly basic oxide, strontia (SrO). SrO nanocrystalline particles have a well-defined shape and exhibit outstanding thermal stability and optical characteristics. Additionally, SrO is a conductor of electricity and has been utilized in solar cells, fuel cells, gas sensors, and solid oxide cathode materials as an oxygen-generating system. Strontium oxides are utilized in a variety of medicinal purposes, such as a substitute for tissue or body components, restorative implant cement, and filling composites. They are employed in catalysis, ceramics, capacitors, and chemical electronics, as well as the manufacture of ferrite ceramic magnets and zinc refining, pyrotechnics and as paint additives.

Materials: Strontium chloride hexahydrate ($SrCl_2 \cdot 6H_2O$, 99%) and sodium hydroxide (NaOH, 98%) were obtained from Sigma-Aldrich while acetic acid ($CH_3COOH$) was purchased from PANREAC QUIMICA SA. Commercially available chitosan (CS) was purchased from Ali Baba Company, China. MBCF, $NaBH_4$ and NaOH were purchased from Sigma Aldrich (Germany).

Figure 1:
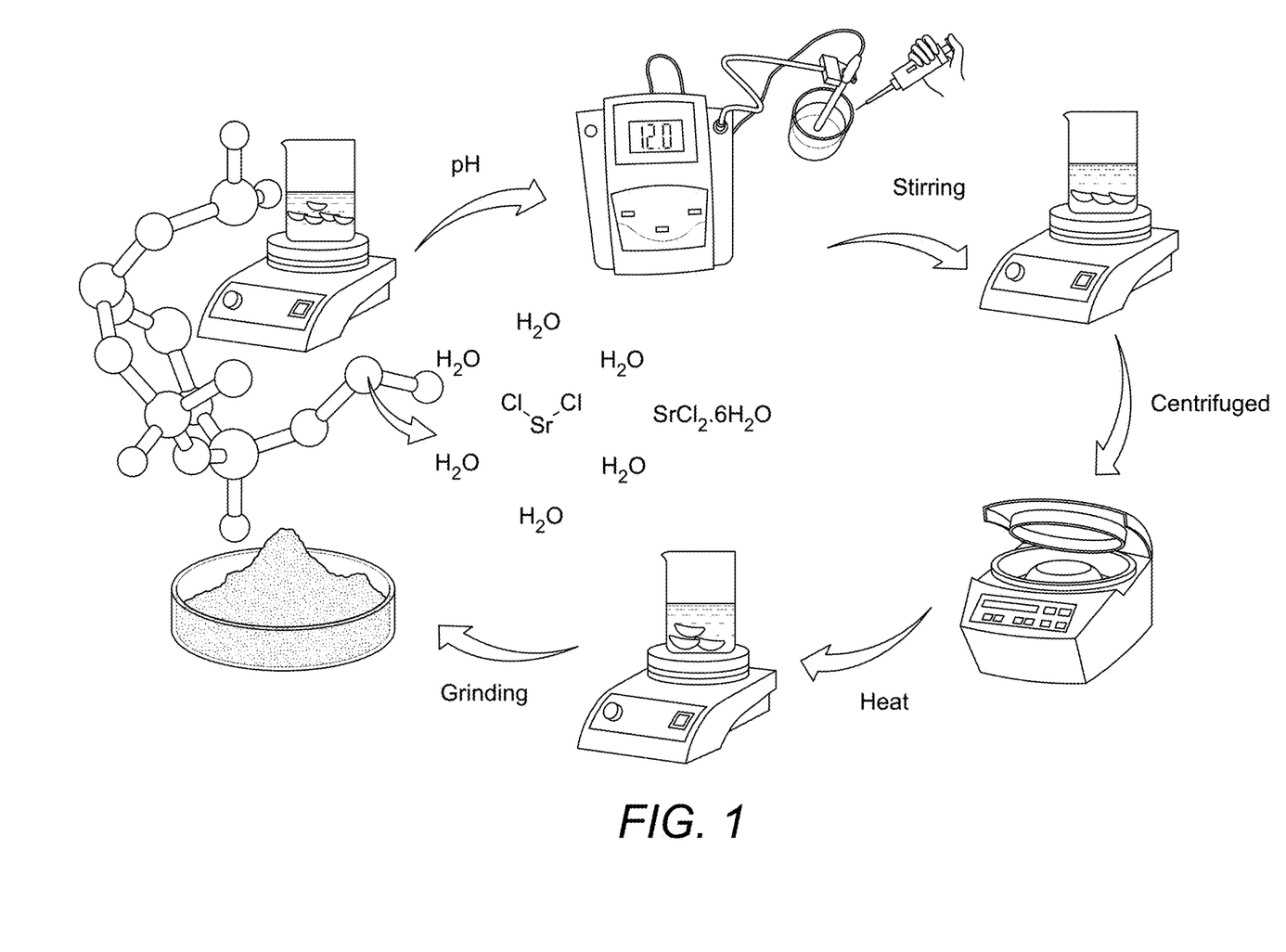
FIG. 1 shows schematic diagram of method of making the CS-doped SrO nanocomposite.
Figure 2:
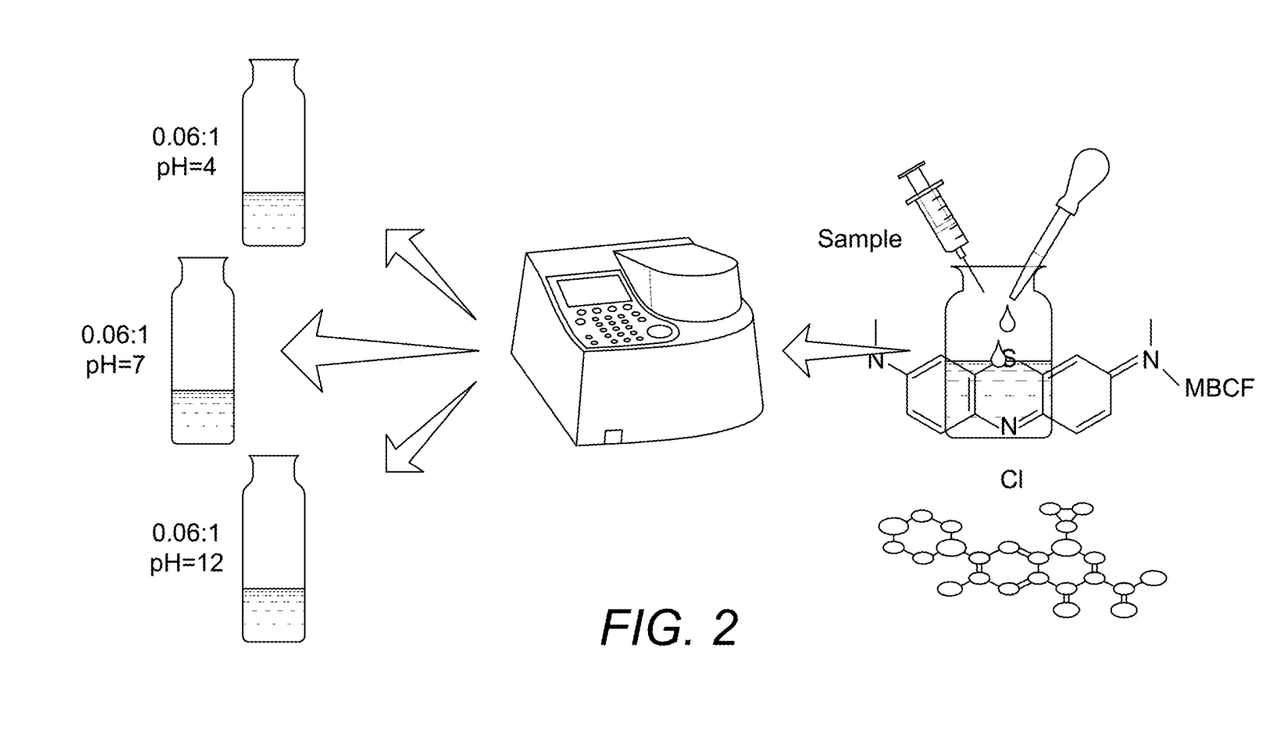
FIG. 2 shows schematic diagram of CS-doped SrO nanocomposite as a catalyst for removing industrial pollutants.

A method and process to synthesize SrO nanoparticles: For SrO nanoparticle synthesis, chemical precursor strontium chloride hexahydrate (0.5 M in 50 ml distilled water) was magnetically stirred for 2 hours. Prepared solution was centrifuged and the supernatant was removed. The collected pellet was washed several times with distilled water to remove the impurities. After centrifugation the supernatant was discarded and the washed precipitate for used for further processing. Subsequently, the washed precipitate was heated at 120° C. for 24 hours to obtain a dry white powder and the powder is grinded to obtain SrO nanoparticles (see FIG. 1)

A method and process to make CS-doped SrO nanocomposite: CS-doped SrO nanocomposite were synthesized by adding various amounts of CS (2, 4, and 6 wt %) in the SrO nanoparticle (0.5 M in 50 ml distilled water) solution. Sodium hydroxide solution (NaOH (0.5M)) was added to the mixed solution to maintain the pH at 12. The NaOH added mixed solution at pH 12 was vigorously stirred at 70° C. for 30 minutes. Finally, the resultant C-doped mixture was centrifuged at 4000 rpm for 10 minutes and collected pellet was dried at 120° C. to obtain chitosan (CS)-doped SrO nanocomposite (CS—SrO nanocomposite).

Isolation and identification of bacteria: Initially, caprine mastitis milk samples clinically positive were evaluated using surf field mastitis test (SFMT). Samples collected from numerous farms of Punjab were streaked on 5% sheep blood agar (SBA). After 48 hours incubation at 37° C., acquired colonies were streaked further on mannitol salt agar and MacConkey agar (MA) in triplets. Purified isolates *Staphylococcus aureus* (*S. aureus*) and *Escherichia coli* (*E. coli*) were obtained. Identification proceeded through Gram's staining, coagulase and catalase tests.

Antibacterial activity: In-vitro bactericidal valuation of CS-doped SrO was directed using Gram-positive (G +ve) *S. aureus* and Gram-negative (G −ve) *E. coli* obtained directly from mastitis milk. Swabbing of sterile petri dishes proceeded with $1.5 \times 10^8$ CFU/ml (0.5 McFarland standard) *S. aureus* and *E. coli* on MSA and MA, respectively. Wells of 6 mm diameter was loaded with (0.5, 1.0 mg/50 µL) of CS-doped SrO in comparison with ciprofloxacin (0.005 mg/50 µL) and 50 µL DIwater used as +ve and −ve controls under aseptic conditions. Bactericidal action considered in terms of inhibition zones diameter (mm) was measured with Vernier caliper after overnight incubation at 37° C. Measured diameters were analyzed statistically by adopting one-way analysis of variance (ANOVA) using SPSS 20.

Characterization of Synthesized CS—SrO Nanocomposite: PAN analytical X-ray diffraction (XRD) equipment with Cu Kα-radiation (λ=0.15 nm) was used to analyze phase composition of prepared CS—SrO nanocomposite within the range of 10°-80°. The presence of bonds in CS—SrO nanocomposite was investigated through FTIR using Perkin Elmer spectrometer. UV-Vis spectrophotometer (Genesys 10S spectrophotometer) was used for optical properties of CS—SrO nanocomposite while PL emission spectra were obtained with JASCO FP-8200 spectrofluorometer. EDS (INCA EDS software) was used to estimate the elemental composition while the morphology and microstructure of CS—SrO nanocomposite were examined with the help of high resolution transmission electron microscope HRTEM (model JEOL JEM 2100F).

Figure 3A:
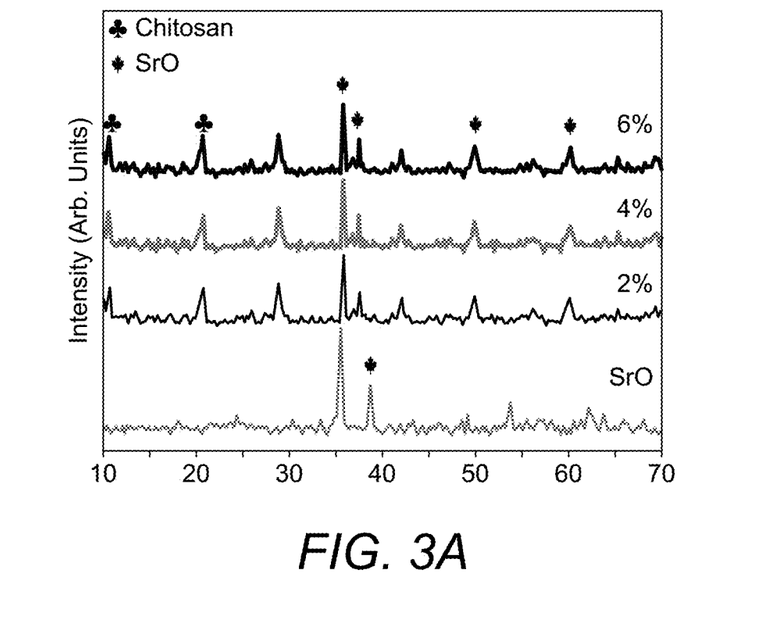
FIG. 3A shows X-ray powder diffraction (XRD) pattern of CS-doped SrO NCs, FIG. 3B Fourier transform infrared (FTIR) spectra, FIG. 3C, FIG. 3D, FIG. 3E.
Figure 3B:
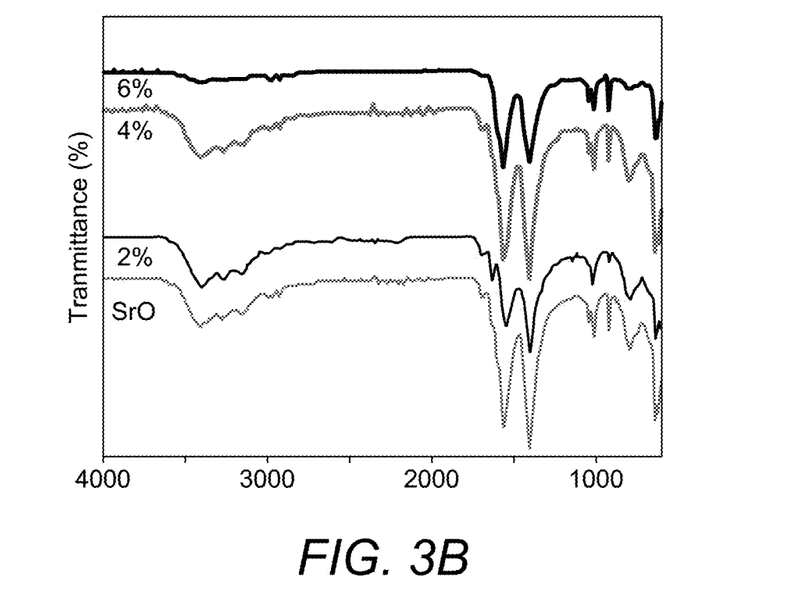
Figure 3C:
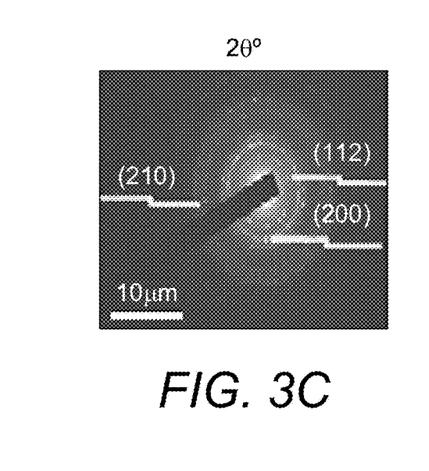
Figure 3D:
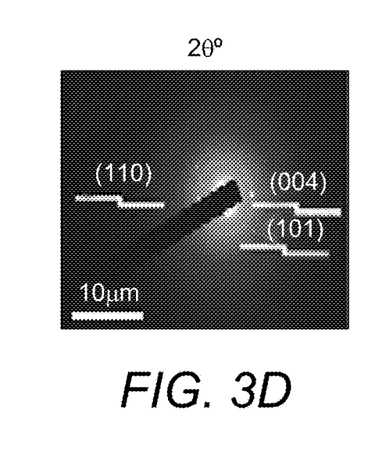
Figure 3E:
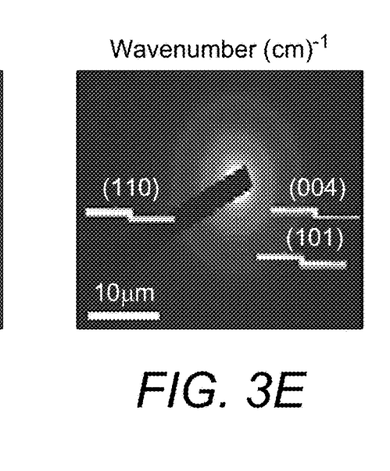
Figure 3F:
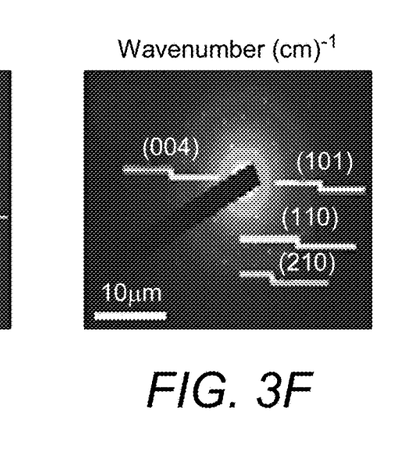
FIG. 3F shows selected area electron diffraction (SAED) pattern of CS-doped SrO nanocomposite (0, 2, 4 and 6 wt %).

Structural properties and phase composition of SrO and CS—SrO nanocomposite were analyzed using XRD technique (FIG. 3A). Observed peaks of reference sample (SrO) found at 35°, 38.6° and 49° assigned to (110), (112) and (210) planes, respectively matched with JCPDS #6-520, 75-0263. Diffraction peaks of CS—SrO nanocomposite demonstrated at 10.1°(001), 20.63°(020), 28.8°(101), 37.4° (101), 42.07°(004), 49.7° (220) and 60.4°(110) are designated using JCPDS file (No: 001-1113, 48-1477 and 01-073-0661) confirming cubic and tetragonal structure of SrO. Average crystallite sizes of samples estimated from Debye-Scherer equation were calculated to be 44.7, 29.18, 29.2 and 29.1 nm for SrO nanoparticles and CS-doped SrO nanocomposite (2, 4 and 6 wt %), respectively (FIG. 3B). Decrease in crystallite size was observed upon varying dopant concentration in SrO. SAED patterns of samples as illustrated in FIG. 3C, FIG. 3D and FIG. 3F. Observed ring features confirm cubic and tetragonal SrO structure, product is crystallized providing evidence that is consistent with XRD results.

Figure 4A:
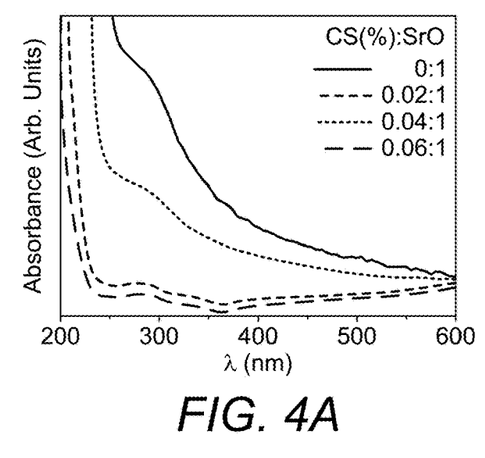
FIG. 4A shows UV vis. Spectra.
Figure 4B:
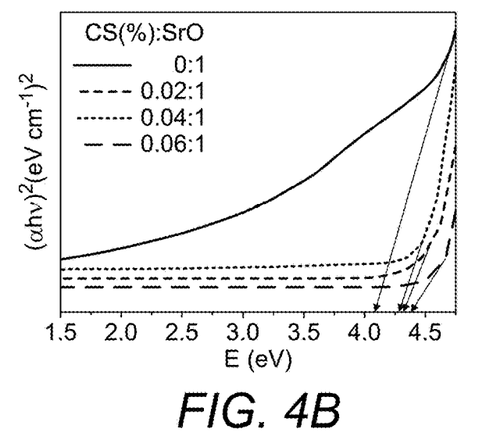
FIG. 4B shows Tauc plot for the band gap and FIG. 4C shows PL spectra from various ratios of CS-doped SrO nanocomposite.

FTIR technique was recorded in the region of 4000-500 cm$^{-1}$ to illuminate functional groups present in the samples (SrO and CS-doped SrO nanocomposite). Observed band at 605 cm$^{-1}$ recognized the formation of metal oxide (Sr—O) bond that confirmed configuration of SrO NCs. Realistic peak at 810.10 cm$^{-1}$ is attributed to Sr—O bending vibrations. Band observed at 1011 cm$^{-1}$ was assigned to Sr—O bond (asymmetric and symmetric vibration frequencies). Absorption band at 1433.11 cm$^{-1}$ can be ascribed to C—O stretching vibrations and O—H bending (14). FTIR spectra of SrO manifested peaks at 3282 cm$^{-1}$ and 1552 cm$^{-1}$ revealed the presence of O—H and —C═C— (stretching), respectively. Broad band at 3422 cm$^{-1}$ indicated the presence of O—H vibrations of water molecules as shown in FIG. 3b. According to UV-visible principle, outer electrons absorbed radiant energy and make transitions to high energy levels. UV-Vis spectra of samples were recorded in the range (200-600 nm) whereas broad absorption band at 296.8 nm was found for the host sample (FIG. 4A). This absorption is attributed to quantum size effect of monodispersed colloidal particles. Upon doping, blueshift was observed from 296.8 to 280 nm attributed to the effect of quantum confinement. This blueshift led to an increase in $E_g$ of SrO (4.19 eV) to 6% doped SrO (4.3 eV)(FIG. 4B).

Figure 4C:
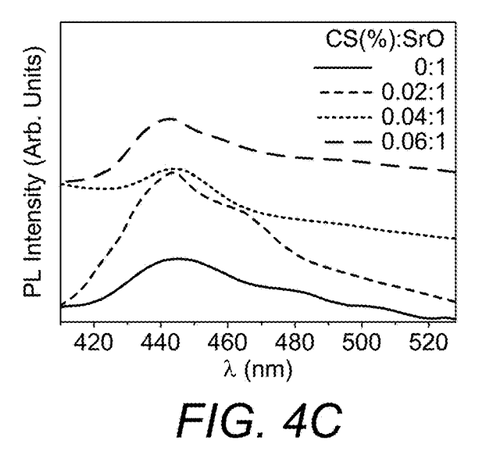

Photoluminescence (PL) spectroscopy was employed to determine migration, transfer, separation and recombination of charge carriers in SrO and CS-doped SrO (FIG. 4C). Results in fast (e$^-$-h$^+$) pairs recombination rate of higher and lower PL intensity may be due to slow (delayed) recombination. PL spectrum indicated peak of SrO at 300 nm with broad emission band in the range of 450-480 nm (blue region) due to excitation recombination and luminescence. CS-doped SrO nanocomposite samples exhibit intense and broad emission bands at around 440 nm (violet region) while decrease in PL intensity was observed for increased doping amount in SrO lattice.

Figure 5A:
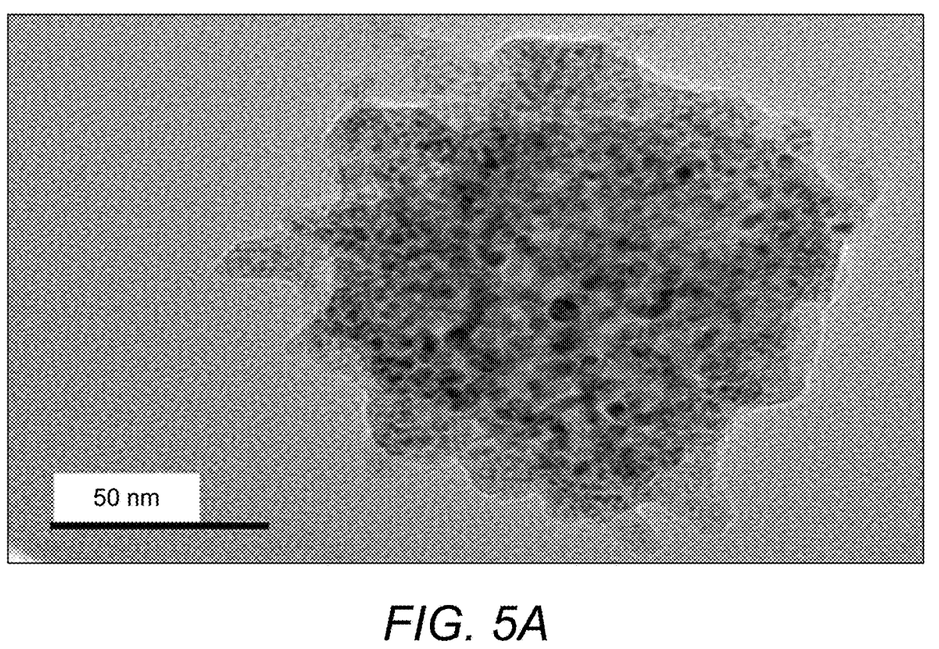
FIG. 5A and FIG. 5B show HR-TEM and d-spacing images of CS:SrO of 0:1, FIG. 5C
Figure 5B:
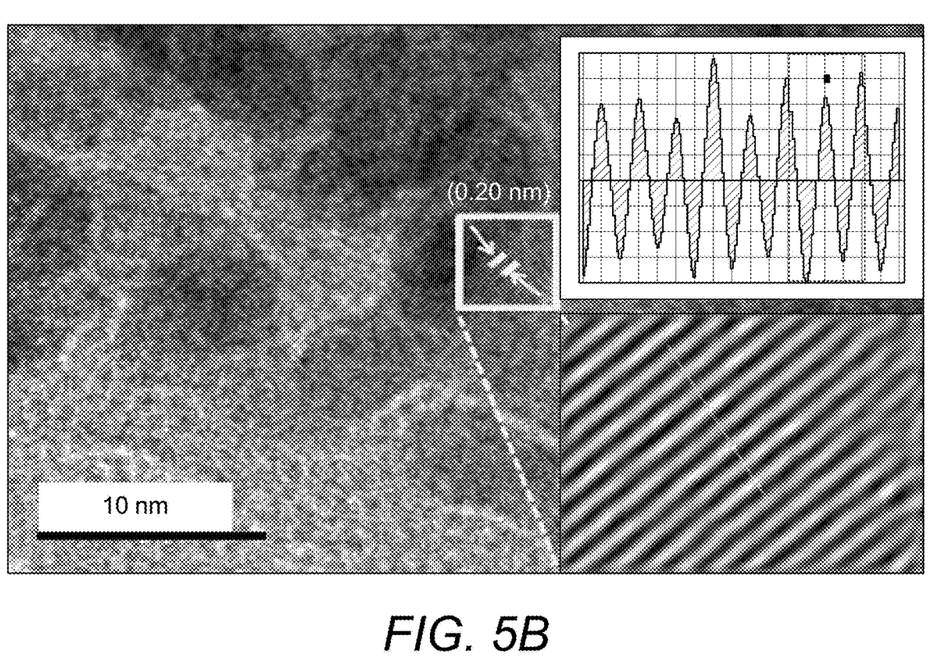
Figure 5C:
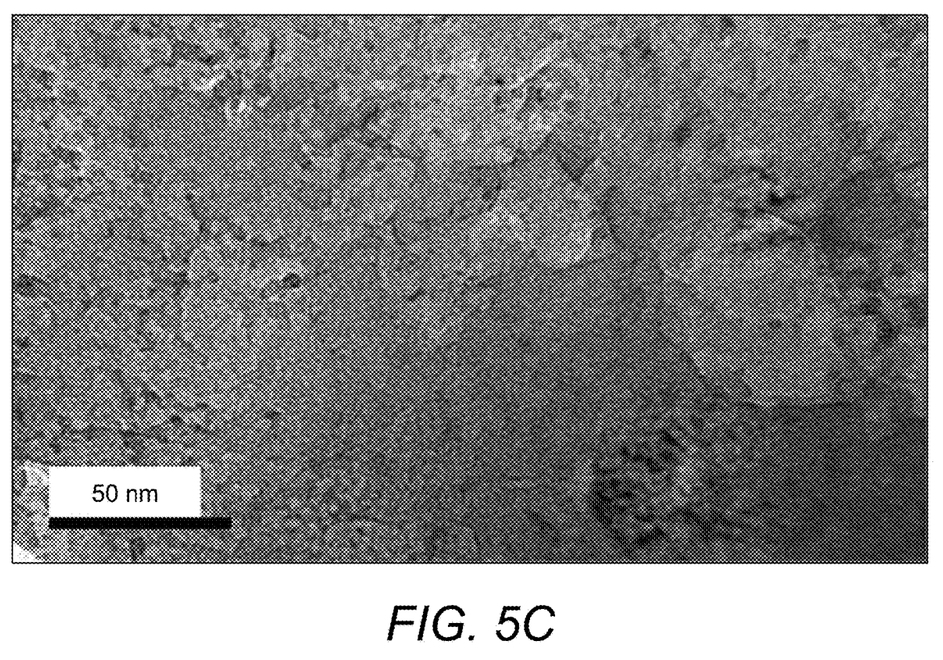
Figure 5D:
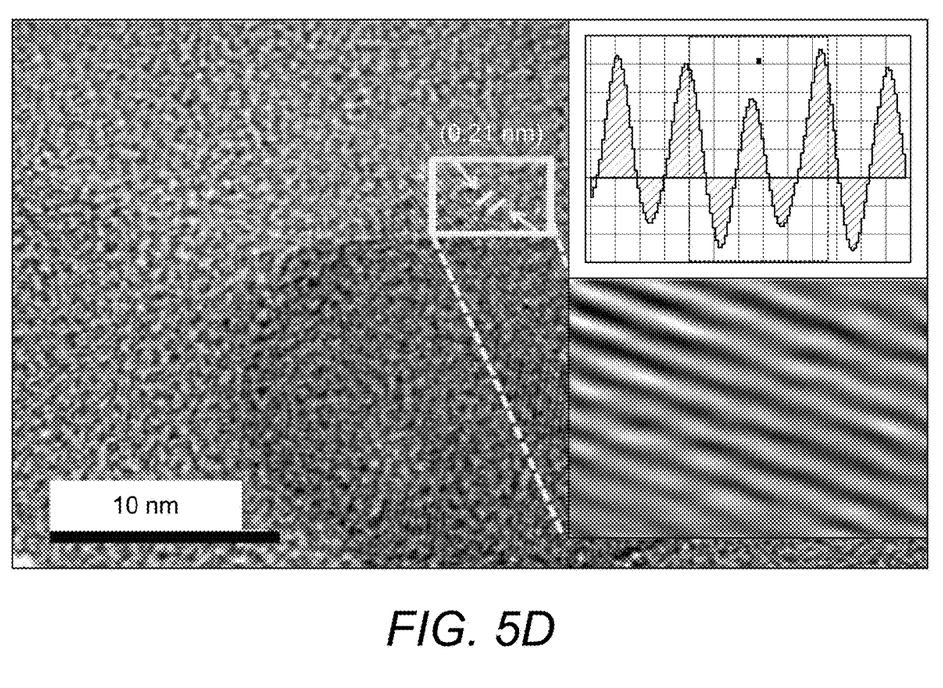
FIG. 5D shows spacing of 0.02:1, FIG. 5E
Figure 5E:
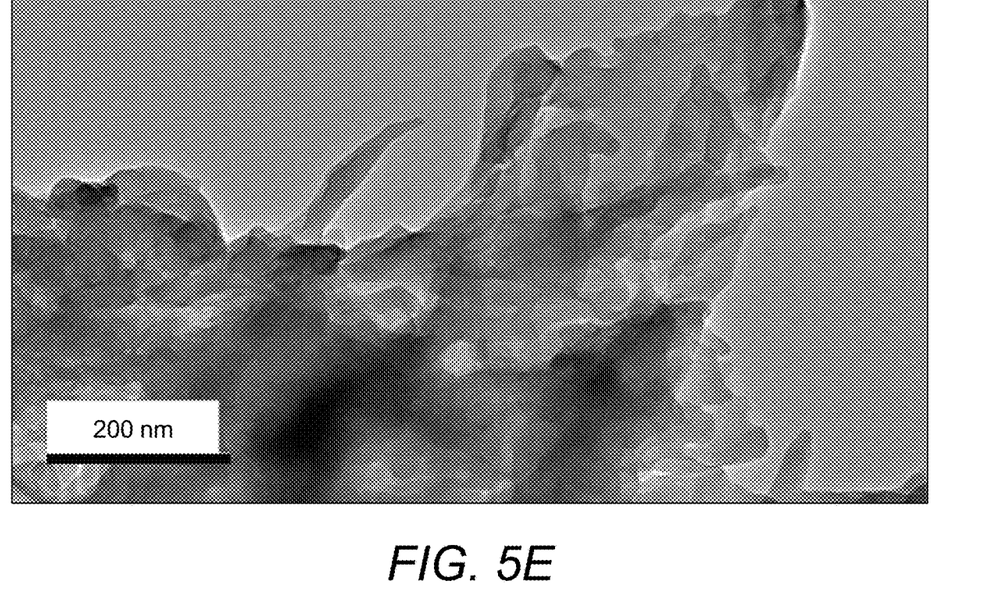
Figure 5F:
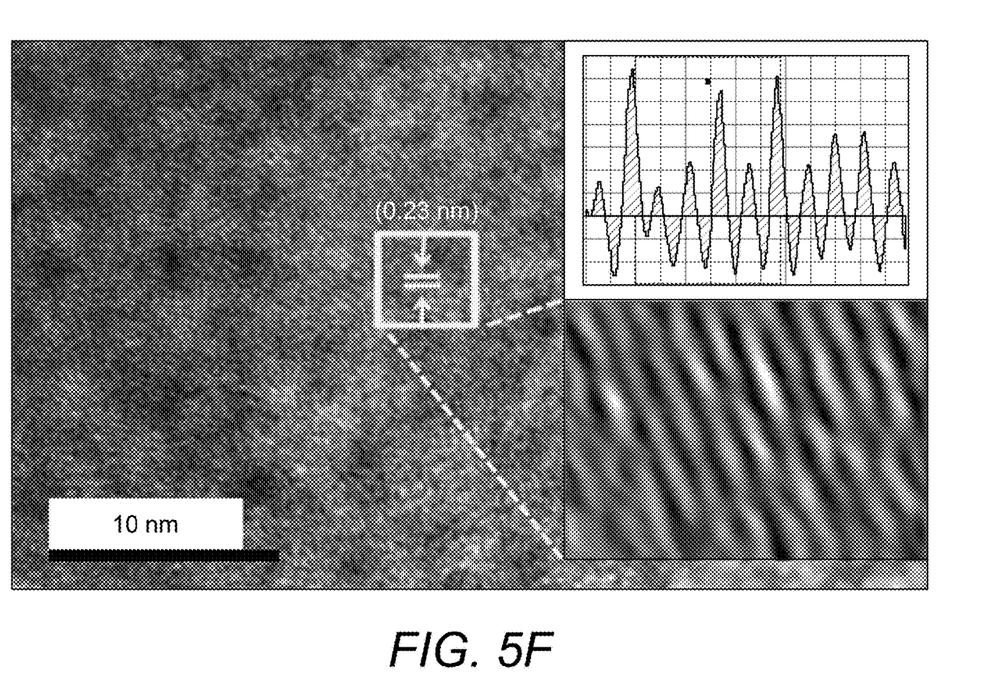
FIG. 5F shows of 0.04:1 and FIG. 5G
Figure 5G:
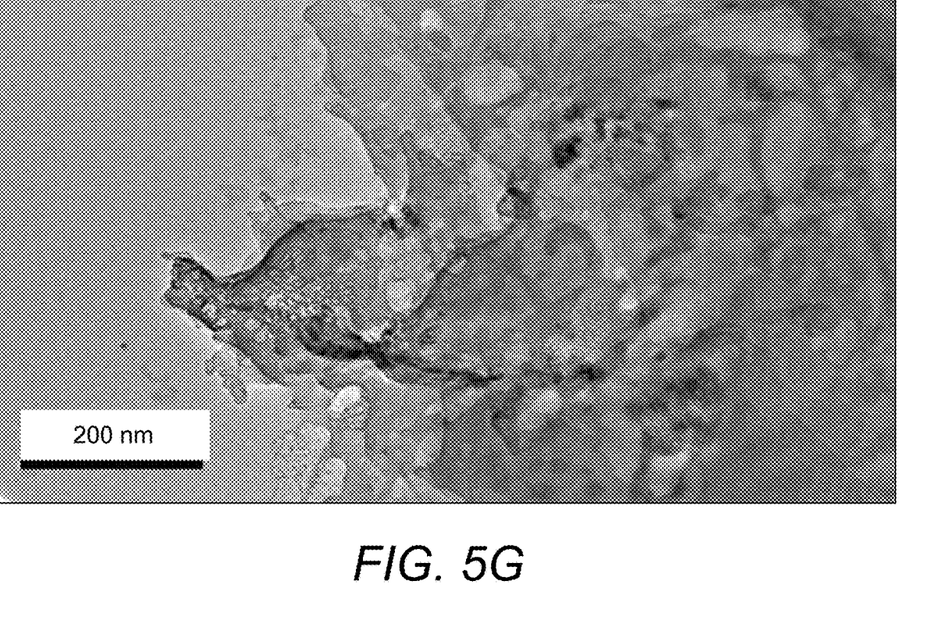
Figure 5H:
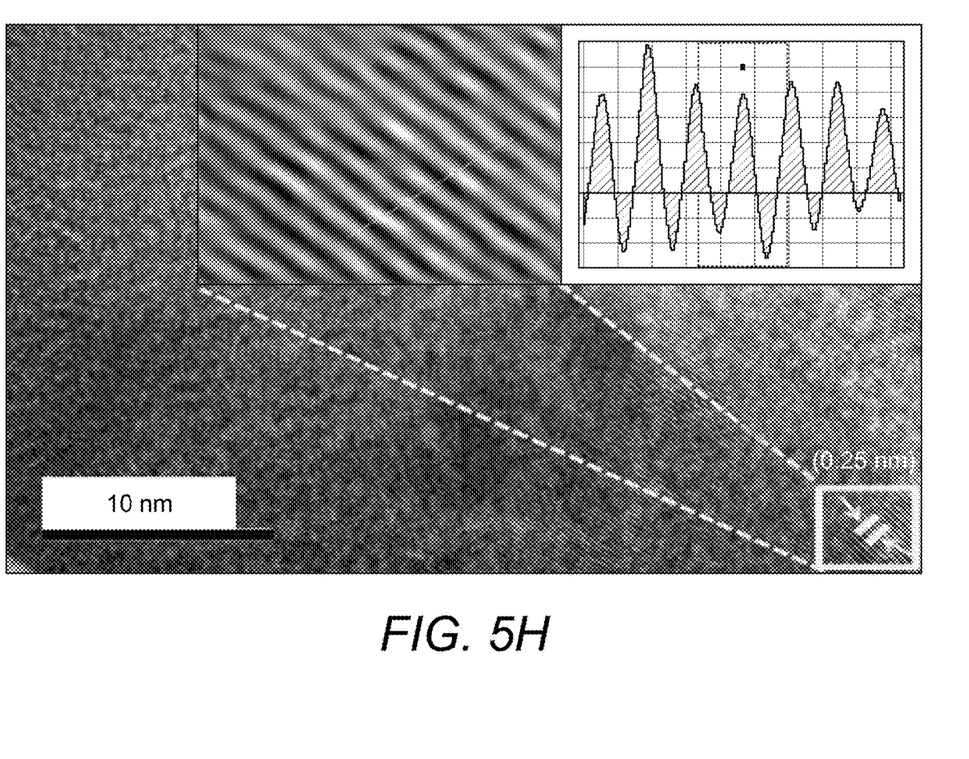
FIG. 5H shows of 0.06:1.
Figure 6A:
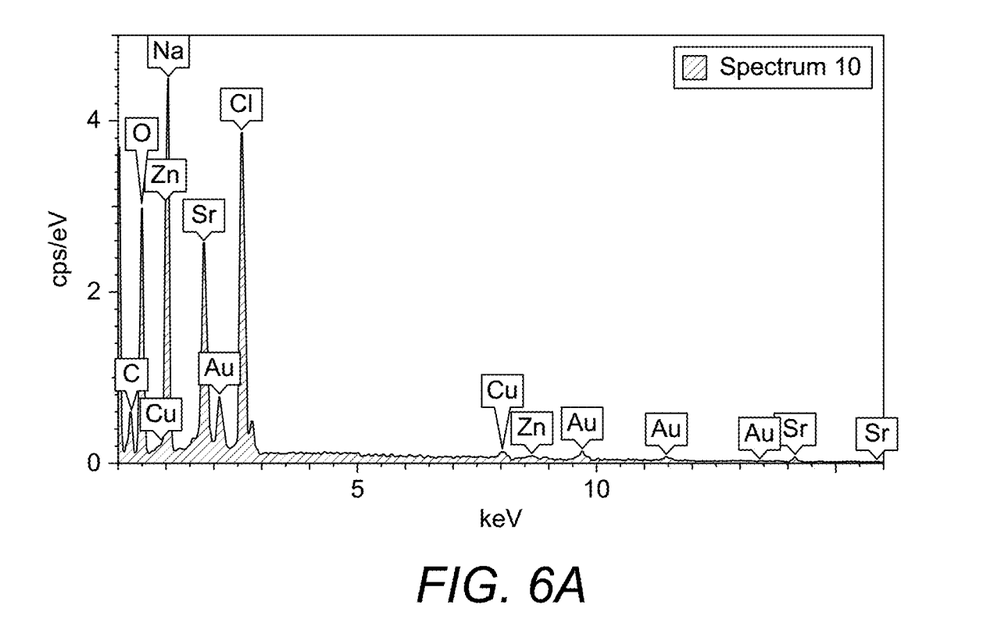
FIG. 6A, FIG. 6B, FIG. 6C and FIG. 6D shows analysis of CS-doped SrO nanocomposite with CS content (2, 4 and 6 wt %).
Figure 6B:
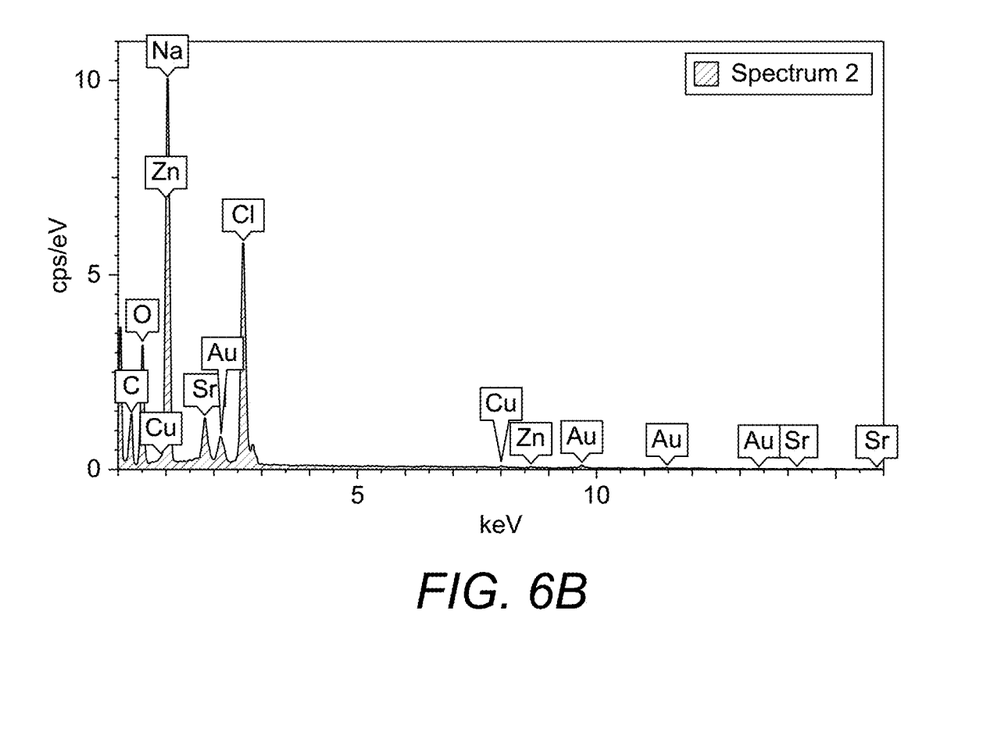
Figure 6C:
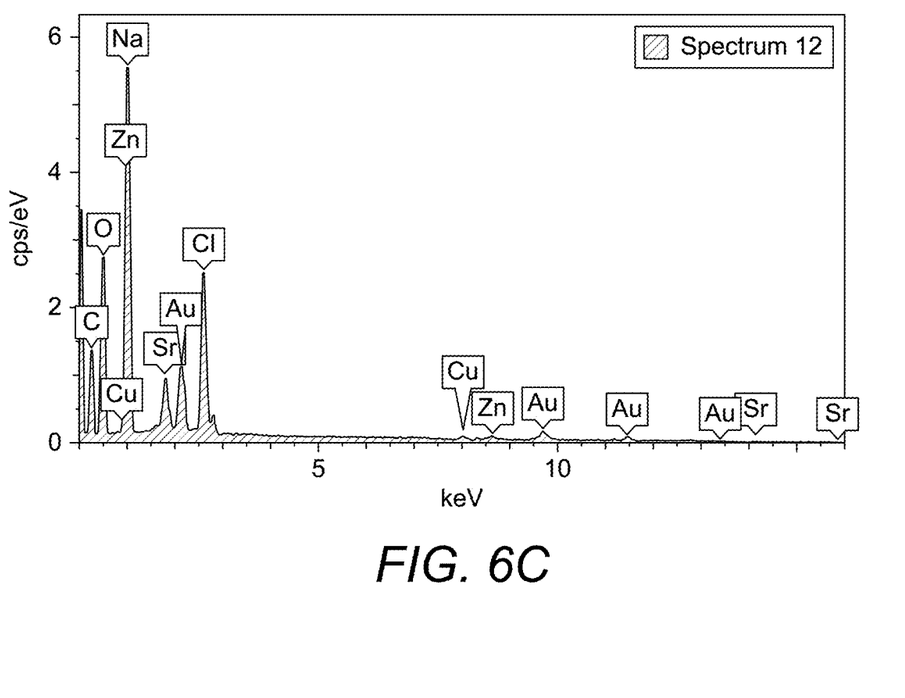
Figure 6D:
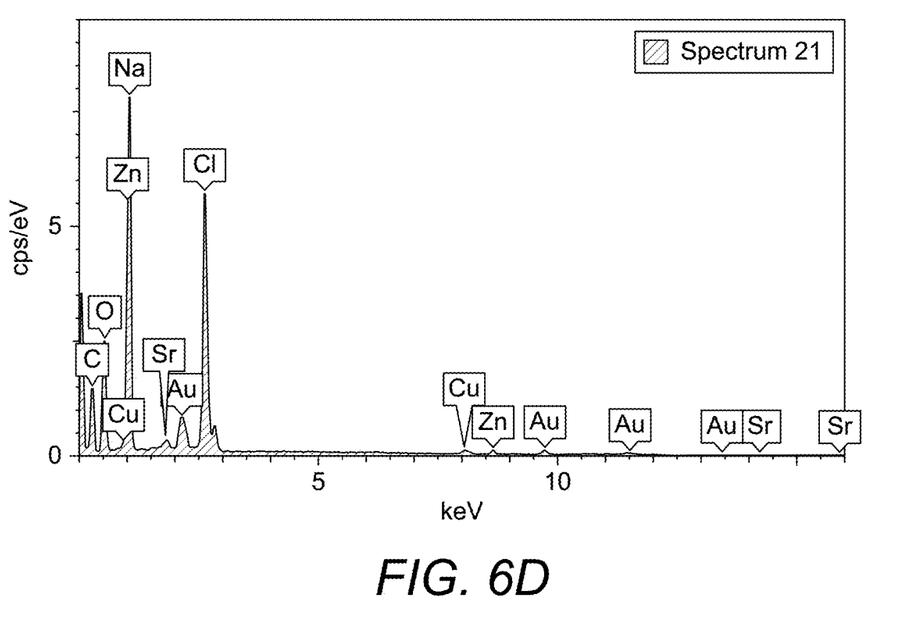

HR-TEM and d-spacing images of CS:SrO (FIG. 5A and FIG. 5B) of 0:1 (FIG. 5C and FIG. 5D) of 0.02:1, (FIG. 5E and FIG. 5F) of 0.04:1 and (FIG. 5G and FIG. 5H) of 0.06:1. HRTEM micrographs depicted the formation of dopant free SrO nanoparticles while porous sheetlike structure embedded with SrO nanoparticles was observed for CS-doped SrO nanocomposite. Agglomeration of SrO nanoparticles was revealed upon increasing doping concentration of CS as depicted in FIG. 4C and FIG. 4D. Confinement of SrO nanoparticles on CS propose a change in $E_g$ edge of material resulting in blueshift in absorption spectra as confirmed by UV-Vis spectra (FIG. 4A). FIGS. 5C, 5D, 5E and 5F images confirmed the formation of agglomerated nanorod-like morphology of doped structures. HRTEM micrographs were used to calculate interlayer d-spacing (FIGS. 5B and 5F) using Gatan software. This was found to be 0.20 nm for SrO and 0.21, 0.23 and 0.25 nm for CS:SrO (2, 4 and 6 wt %) respectively, which matched well with XRD results. Meanwhile, dopant effect on the change in d-spacing is also clear.

FIG. 6A, FIG. 6B, FIG. 6C and FIG. 6D show analysis of CS—SrO nanoparticles with CS content ranging from 2, 4 and 6 wt %. Elemental composition of SrO nanoparticles and CS-doped SrO nanocomposite has been determined by EDS which confirmed the presence of metal and oxygen components in SrO nanoparticles. EDS analysis indicated 1:1 composition of Sr and O along with other impurities such as Na, and Zn. Peaks of gold (Au) originated from coating sputtered on the samples to prevent charging during SEM analysis. Carbon and oxygen signals in doped samples depicted successful incorporation of CS in SrO (FIGS. 6 b-d).

TABLE 1

Antimicrobial activity of CS-doped SrO nanocomposite:

| Sample | [1]Inhibition zone (mm) | | [2]Inhibition zone (mm) | |
|---|---|---|---|---|
| | 0.5 mg/50 μL | 1.0 mg/50 μL | 0.5 mg/50 μL | 1.0 mg/50 μL |
| SrO | 0 | 0.95 | 0 | 0.9 |
| CS-SrO 2% | 0 | 0 | 0 | 5.30 |
| CS-SrO 4% | 0 | 0 | 2.85 | 6.35 |
| CS-SrO 6% | 0 | 9.20 | 3.45 | 7.05 |
| Ciprofloxacin | 9.25 | 9.25 | 7.15 | 7.15 |
| DIW | 0 | 0 | 0 | 0 |

[1]Inhibition zones (mm) measured for *S. aureus*
[2]Diameters (mm) observed for *E. coli*

In-vitro, antimicrobial efficacy of C-doped SrO nanocomposite (0, 0.02, 0.04 and 0.06 wt %) was evaluated with inhibition zones measurements (mm) against *S. aureus* and *E. coli* through well diffusion method as presented in Table 1. The results indicated synergistic response of inhibition zones and concentrations of C-doped SrO nanocomposite. Statistically significant inhibition recorded for *S. aureus* ranged (0.95-9.20 mm) at high concentrations for C-doped SrO nanocomposite and (0-3.45 mm) and (0.9-7.05 mm) for low and high concentrations, respectively against *E. coli*. All obtained results compared with +ve (7.15 and 9.25 mm) and –ve control (0 mm). The efficacy % age perceived (0-99.4%) for *S. aureus* at high concentration while (0-48.2%) and (12.5-98.6%) against *E. coli* for both concentrations, respectively. Overall, CS(2 and 4%)-doped SrO nanocomposite showed null bactericidal efficacy against G +ve (*S. aureus*) compared with G–ve (*E. coli*) at high and low concentrations as shown in Table 1 while, doped SrO (0 and 6 wt %) showed significant antibacterial activity against both bacteria.

Figure 7:
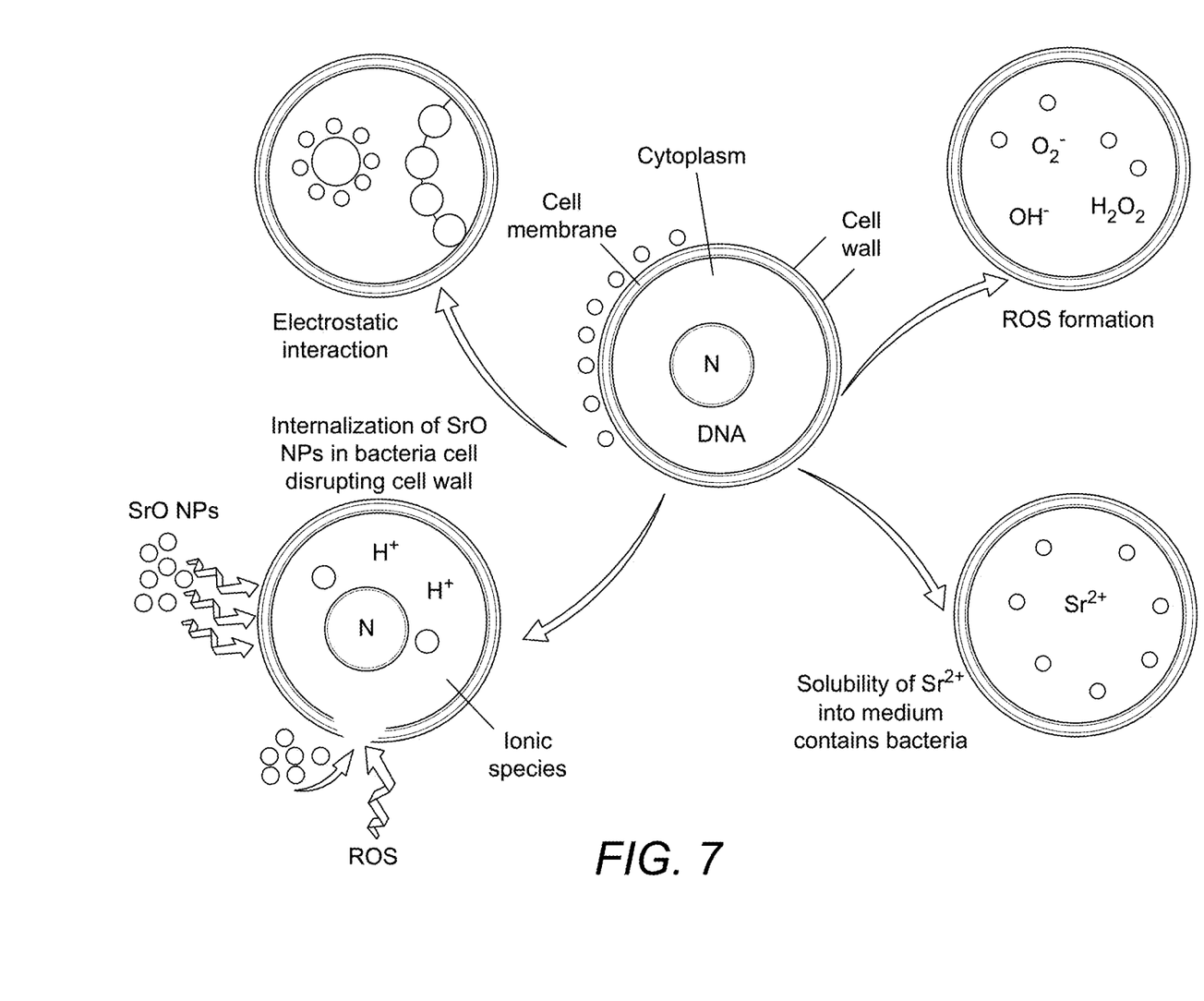
FIG. 7 shows various possible mechanisms of SrO—NPs antibacterial activity, including ROS formation, $Sr^{2+}$ release, internalization of SrO—NPs into bacteria.

C-doped SrO nanocomposite's size and concentration affect bactericidal action since size of nanocomposite converses antimicrobial activity. Reactive oxygen species efficiently produced by C-doped SrO nanocomposite's enclose bacterial outer membrane resulting cell death via extrusion of cytoplasmic contents. Various factors i.e., shape, size and concentration of fabricated material depict significant role in antibacterial action of fabricated structures. Between bacterial isolates, an electrostatic interface produced by C-doped SrO nanocomposite's results in the efficient generation of ROS responsible for bacteria death (FIG. 7). Other mechanisms found significant for C-doped SrO nanocomposite's bactericidal mechanism includes cationic interaction of Sr$^{2+}$ with bacteria cell –ve parts resulting in their collapse.

INDUSTRIAL APPLICABILITY

CS-doped SrO nanocomposite were successfully synthesized through co-precipitation route for catalytic activities. Effect of CS doping on SrO nanoparticle resulting in CS-doped SrO nanocomposite morphological features, optical properties, elemental composition and phase constitution were analyzed. XRD analysis confirmed tetragonal and cubic structures of SrO nanoparticles and CS-doped SrO nanocomposite. UV-vis spectroscopy was used to obtain 4.19 eV of SrO nanoparticles while emission spectra of CS-doped SrO nanocomposite showed blueshift upon CS doping with multi-concentration. Interlayer d-spacing attained from HRTEM micrographs well matched with XRD d-spacing. Purity content of prepared nanocomposites was measured with EDS analysis. Extent of nanoparticle formation increased upon doping which served to enhance the catalytic activity. Inhibition of bacterial growth was seen by adding CS-doped SrO nanocomposite.

What is claimed is:

1. A method, comprising;
dissolving a strontium chloride hexahydrate in water and stirring the solution for 2 hours to make a dissolved solution of the strontium chloride hexahydrate;
adjusting a pH of the dissolved solution of strontium chloride hexahydrate to a specific pH by adding sodium hydroxide solution for 2 hours to form a precipitate of a strontium chloride hexahydrate nanoparticle in solution;
centrifuging a strontium chloride hexahydrate nanoparticle in solution to collect a pellet of the precipitate of the strontium chloride hexahydrate nanoparticle;
heating the pellet of the strontium chloride hexahydrate nanoparticle at 120° C. for 24 hours and grinding the heated pellet to obtain a powder of strontium chloride hexahydrate nanoparticles;
preparing a strontium chloride hexahydrate nanoparticle solution using the powder of strontium chloride hexahydrate nanoparticles in distilled water with various concentrations of a chitosan the specific pH using a specific basic solution to create a chitosan (CS)-doped Strontium oxide (SrO) nanocomposite; and
inhibiting a bacterial growth by adding the CS-doped SrO nanocomposite in a cell infected with a bacteria.

2. The method of claim 1, wherein the specific basic solution is sodium hydroxide at 0.5M strength.

3. The method of claim 1, wherein the bacteria is one of a *S. aureus* and *E. coli*.

4. The method of claim 1, wherein the specific pH is 12.

5. The method of claim 1, wherein the centrifugation is done at 4000 rpm for 10 minutes.

6. The method of claim 1, wherein the bacterial growth is for a of G+ve and G−ive bacteria.

7. The method of claim 1, wherein the specific concentration of chitosan is one of a 2%, 4%, and 6%.

8. A process of making a chitosan (CS)-doped Strontium oxide (SrO) nanocomposite, consisting of;
mixing water and a strontium chloride hexahydrate and stirring the mixer for 2 hours to make a solution of the strontium chloride hexahydrate;
forming a precipitate of a strontium chloride hexahydrate nanoparticle in solution by adjusting a pH of the solution of strontium chloride hexahydrate to a specific pH by adding sodium hydroxide solution for 2 hours and stirring;
collecting a pellet strontium chloride hexahydrate nanoparticle by centrifuging a strontium chloride hexahydrate nanoparticle in solution;
making a powder of strontium chloride hexahydrate nanoparticles by heating the pellet of the strontium chloride hexahydrate nanoparticle at 120° C. for 24 hours;
preparing a strontium chloride hexahydrate nanoparticle solution using the powder of strontium chloride hexahydrate nanoparticles in distilled water with various concentrations of a chitosan the specific pH using a specific basic solution to create a CS-doped SrO nanocomposite; and
inhibiting a bacterial growth by adding the CS-doped SrO nanocomposite in a bacteria in an infected cell.

9. The process of claim 8, wherein the specific basic solution is sodium hydroxide at 0.5M strength.

10. The process of claim 8, wherein the bacteria is one of a *S. aureus* and *E. coli*.

11. The process of claim 8, wherein the specific pH is 12.

12. The process of claim 8, wherein the centrifugation is done at 4000 rpm for 10 minutes.

13. The process of claim 8, wherein the bacterial growth is for a of G+ve and G−ive bacteria.

14. The process of claim 8, wherein the specific concentration of chitosan is one of a 2%, 4%, and 6%.

* * * * *